United States Patent [19]

Kramer

[11] Patent Number: 5,746,061
[45] Date of Patent: May 5, 1998

[54] PHYSCHROMETRIC MEASUREMENT OF AIR FLOW THROUGH AIRCONDITIONING EVAPORATOR

[76] Inventor: Daniel E. Kramer, 2009 Woodland Dr., Yardley, Pa. 19067

[21] Appl. No.: 915,336

[22] Filed: Aug. 19, 1997

Related U.S. Application Data

[60] Provisional application No. 60/027,048, Sep. 30, 1996.
[51] Int. Cl.[6] .................................................. F25B 49/00
[52] U.S. Cl. ........................... 62/127; 62/130; 73/204.11; 374/39
[58] Field of Search ............................. 62/125, 126, 127, 62/128, 130, 129; 165/11.1; 374/40, 39; 73/861, 204.11, 204.13, 204.16

[56] References Cited

U.S. PATENT DOCUMENTS

| | | | |
|---|---|---|---|
| 4,611,470 | 9/1986 | Enström | 62/127 |
| 4,768,346 | 9/1988 | Mathur | 62/127 |
| 5,026,171 | 6/1991 | Feller | 374/40 X |
| 5,435,146 | 7/1995 | Clark | 62/130 X |
| 5,645,348 | 7/1997 | Stulen et al. | 73/204.11 |

*Primary Examiner*—Harry B. Tanner
*Attorney, Agent, or Firm*—Daniel Kramer

[57] ABSTRACT

A method for determining airflow through an air cooling and dehumidifying coil by measuring the condensate rate and the moist air conditions entering and leaving the coil. The mass air flow, the volume air flow and the cooling capacity are then calculated from data exhibited on a psychrometric chart or by calculating the same result from basic principles.

7 Claims, 2 Drawing Sheets

PSYCHROMETRIC CHART (simulation)

5,746,061

PHYSCHROMETRIC MEASUREMENT OF AIR FLOW THROUGH AIRCONDITIONING EVAPORATOR

This application claims the benefit of U.S. Provisional application Ser. No. 60/027,048, filed Sep. 30, 1996.

FIELD OF THE INVENTION

The present invention relates to the science of psychrometry. That is, the characteristics of moist air and measurements is pertaining thereto. The invention further relates to the use of psychrometric measurements to measure the air flow through a cooling and dehumidifying heat transfer element.

BACKGROUND OF THE INVENTION

In large buildings with many chilled water or direct expansion coils, issues can arise concerning the air flow through and cooling effect of a given coil compared with its calculated or predicted performance. The most effective resolution of such issues would be the actual measurement of the mass air-flow through the coil and its cooling capacity.

Known techniques for such capacity measurements involved measurement of the water flow rate and temperature change (Delta T) through the specific coil at issue. However, calculation based on such coolant flow/Delta T measurements did not provide air flow.

Further, installation of water flow instruments involved breaking into the water lines, possibly interfering with cooling in other parts of the system.

Resolution of such capacity and air flow problems, therefore, frequently generated such significant issues that litigation resulted.

The method of the invention disclosed herewith provides means for determination of both the mass and the volume air flow and the actual cooling capacity of a dehumidifying coil without measurement of any of the refrigerant side parameters. The only data required or such determination are psychrometric conditions of the air entering and leaving the cooling coil and the flow rate of the wager condensate condensed from the air stream by the cooling effect of the cooling medium.

SUMMARY OF THE INVENTION

A method for determining airflow through an air cooling and dehumidifying coil, said coil having a condensate rate and said coil further having an air stream traversing it and said coil exhibiting a cooling effect on said air stream, said air stream having an inlet condition characteristic of its moisture content before having traversed the coil, an outlet condition characteristic of its moisture content after having traversed the coil and a mass flow, said method comprising the steps of:

determining the condensate rate, determining the inlet condition, determining the outlet condition and calculating the mass air flow from the inlet condition, the outlet condition and the condensate rate.

BRIEF DESCRIPTION OF THE DRAWINGS

The foregoing summary as well as the following description of preferred embodiments of the invention, will be better understood when read in conjunction with the appended drawings. For the purpose of illustrating the invention there are shown in the drawings embodiments which are presently preferred, it being understood, however, that the invention is not limited to the specific instrumentalities or the precise arrangement of elements or process steps disclosed.

DETAILED DESCRIPTION OF THE INVENTION

The psychrometric measurement of the capacity of a cooling and dehumidifying coil requires knowledge of the enthalpy of the air entering and the air leaving the coil and the mass air-flow.

In addition to atmospheric pressure, the enthalpy of moist air can be calculated or read from a combination of parameters such as dry-bulb temperature plus wet-bulb temperature or relative humidity plus (try-bulb temperature or dew-point temperature plus relative humidity or from any other combination of parameters which define a discrete location on the psychrometric chart.

The humidity ratio is a moist air characteristic defined as mass of water vapor in a unit of dry air divided by the mass of that unit of dry air. Any combination of parameters which defines a discrete location on the psychrometric chart at a given atmospheric pressure, or its algebraic equivalent, will also allow the humidity ratio to be determined. The dew point temperature alone is sufficient.

Instruments are readily available which will sense and remotely display or provide analog or digital output for dry-bulb temperature, wet bulb temperature, dew point temperature and relative humidity.

Having determined the location of the entering and leaving air conditions on the psychrometric chart, and measured the rate at which condensate is produced by the cooling coil and its temperature, the mass air-flow and capacity can be calculated.

Inch-pound (IP) units are used throughout this article since any set of consistent unit will serve to illustrate the procedure. ASHRAE Handbooks published in SI units are available for those wishing to adapt these procedures and the formulae referenced herein to the SI system.

Figure 1:
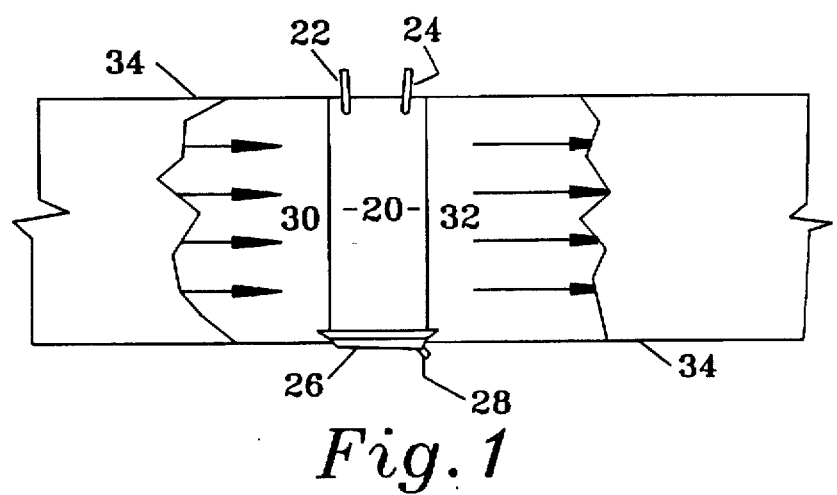
FIG. 1 is a side elevation of an embodiment of the present invention showing a cooling and dehumidifying coil 20 installed in a duct with a condensate collecting pan and drain outlet.

Referring now to FIG. 1, showing a side elevation of a duct partly cut away to show a cooling and dehumidifying coil 20 installed in a duct with a condensate collecting pan and drain outlet 34. Coolant inlet 22 and coolant outlet 24 are provided for supplying a cold fluid to cooling coil 20. The coolant may be a cold volatile refrigerant or a chilled water or brine. There is provided on the air inlet side of the coil means 30 for measuring the psychrometric conditions of the air about to enter coil 20 and on the air outlet side of the coil means 32 for measuring the psychrometric conditions of the leaving air. Means 28 are provided for measuring the flow rate of the condensate condensed out of the air flowing through the cooling coil and transiting condensate drain pan 26.

To illustrate the air flow measurement process, there is an entering air-stream to the cooling coil having a 90° F. dry-bulb temperature and a 74.8 wet-bulb temperature.

These temperatures are measured by means 30 positioned just as the air stream enters cooling coil 20. At measuring means 32 the air-stream leaving the cooling coil has a 55° F. dry-bulb and 53.4 wet-bulb temperature.

All the condensate emitted by the coil over a 20 minute period has been carefully collected and found to weigh 80 ounces with 60° F. temperature. Condensate flow measuring means 28 may be employed for this purpose.

Figure 2:
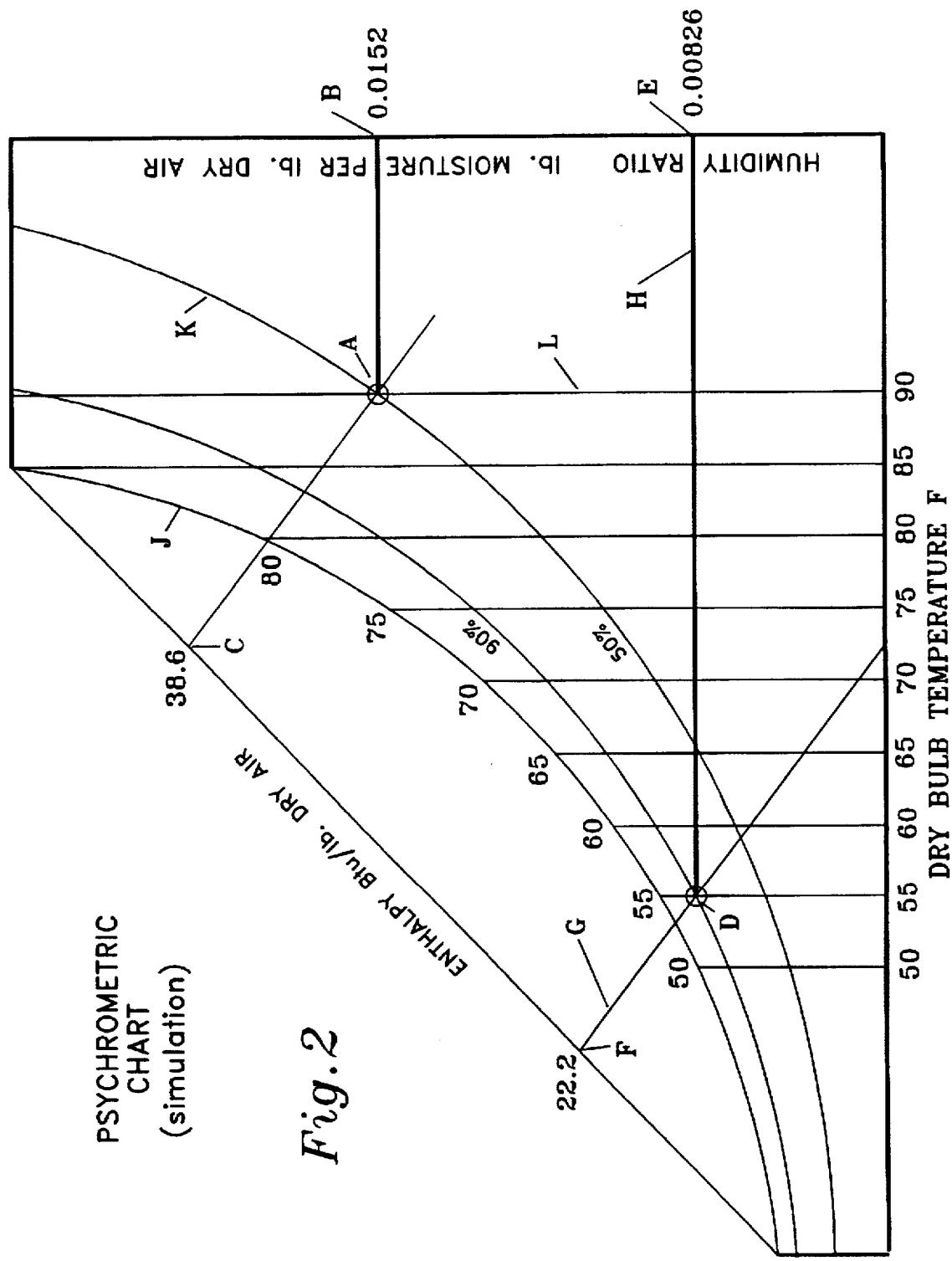
FIG. 2 is a representation of a psychrometric chart displaying the interaction of the various properties of moist air whereby the measured data is converted into the desired values of air mass flow, air volume flow and capacity.

Table 1 summarizes the observed data. FIG. 2 displays a sea level psychrometric chart abstracted from the 1993 ASHRAE Handbook of Fundamentals on which are circled at "A" the entering and at "B" the final air stream conditions recorded above.

It should be noted that the positions of points A and B can be located also by measurements other than wet bulb and dry bulb temperatures, at least the following data pairs can be employed for this purpose:

Dry bulb (line L) and dew point (line H) temperatures;
Dry bulb temperature and relative humidity (line K);
Dew point (h) and wet bulb (G) temperatures;
Wet bulb temperature (G) and relative humidity (K).

Therefore, it is the intent of this disclosure not to restrict the measurement or calculation means by which the humidity ratios and enthalpies of the entering and leaving air streams are determined since it may be possible to determine such values by direct measurement.

TABLE 1

DATA OBSERVED FROM COOLING COIL 20, FIGURE 1:

| | Entering Air | Final Air |
| --- | --- | --- |
| Dry-Bulb t F | 90 | 55 |
| Wet-Bulb tw F | 74.8 | 53.4 |

Condensate collected: 80 ounces/20 minutes = 15 lb/hr.

TABLE 2

DATA READ FROM FIGURE 2

| | Entering Air | Final Air |
| --- | --- | --- |
| Relative Humidity RH | 50% | 90% |
| Enthalpy h Btu/lb Dry Air (DA) | 38.6 | 22.2 |
| Humidity Ratio W lb moisture/lb DA | 0.01515 | 0.00826 |
| Volume v Cu-ft/lb DA | 14.19 | |

The mass flow m of air in pounds per hour is calculated at equations 1 and 2 simply by subtracting the leaving humidity ratio from the entering humidity ratio and dividing this difference into the mass condensate rate in pounds per hour.

$$m \text{ lb/hr air flow} = \frac{15 \text{ lb/hr condensate}}{(0.0152 - 0.00826)} \quad \text{Eq. 1}$$

$$\frac{15}{0.00694} = 2161 \text{ lb/hr Dry Air} \quad \text{Eq. 2}$$

The volumetric air flow in cubic feet per minute (cfm) is calculated at equations 3 and 4 by multiplying the mass air flow, calculated at equations 1 and 2, by the specific volume in cubic feet per pound and dividing the result by 60.

$$\text{Cubic ft/min=cfm=lb/hr}\times\text{cu-ft/lb /60} \quad \text{Eq.3}$$

$$=2161\times14.19 / 60 = 511 \text{ cfm} \quad \text{Eq.4}$$

The cooling effect of the cooling coil on the air traversing it is calculated at equation 5 by multiplying the enthalpy change in the air as it passes over the evaporator, (38.6–22.2), by the mass flow of the air evaluated at equations 1 and 2. Employing the data from table 2, values read directly from the psychrometric chart, the following derives:

$$\text{Btu/hr}=(38.6-22.2)\times2161=16.4\times21614=35440 \text{ Btu/hr} \quad \text{Eq.5}$$

While the cooling effect on the air is 35.440 Btu/hr, the load on the cooling coil is somewhat greater, since it has condensed and cooled the condensate. The enthalpy of the 60° F. condensate (above the 32° F. datum) is 28 Btu/lb. for a total condensate enthalpy of:

$$28\times15=420 \text{ Btu/hr.} \quad \text{Eq.6}$$

Therefore the total cooling effect provided by the cooling coil is:

$$35,440+420=35,860 \text{ Btu/hr.} \quad \text{Eq.7}$$

It should be noted that the ASHRAE psychrometric chart illustrated alcove has been calculated and designed for predicting moist air relationships only at sea-level atmospheric pressure of 29.92 inches Mercury (101.4 KPa). ASHRAE also publishes psychrometric charts for 5000 feet elevation (Chart #4 @ 24.89 in. Hg.:83.1 KPa) and for 7500 feet elevation (Chart #5 @ 22.65 in. Hg.:76.5 KPa).

Where the atmospheric pressure is different from those provided by the psychrometric charts or where computer computation of air flow and capacity from digital data inputs is desired, procedures for performing the calculations can be found in Chapter 6 of the ASHRAE 1993 Handbook of Fundamentals (HOF) and are illustrated below.

For this example, it is assumed that there is available an instrument that provides a digital output of relative humidity (RH) and dry-bulb temperature in degrees F (t) and that the same entering and leaving air conditions and condensate rate apply as set forth in the above example.

The calculation route to the desired results of air flow and capacity are not as clear as in the above described case employing the psychrometric chart.

We must first calculate the saturation pressure of water ps at the entering and leaving air temperatures. Then we must calculate the partial pressure of water pw in the air. Only then, knowing the atmospheric pressure in "Hg, can we calculate the desired humidity ratios W which we employ for the mass air flow calculations performed in the chart case described above.

Further, to secure capacity and volume air flow from the mass air flow we must also calculate air specific volume and air enthalpies.

ASHRAE's Handbook of Fundamentals in Table 3 of Chapter 6, pages 6.6 through 6.10 (HOF 6.6–6.10), provides the saturation pressure ps of water over the temperature range of −80° F. through 300° F.

The value of ps can be read from table 3 or calculated by the polynomial provided there (HOF 6.11 Eq.3) which provides the natural logarithm of ps to six significant figures in psia employing absolute temperature T as input variable.

However, since most thermometers and RH meters promise no more than plus or minus one percent accuracy, and since we are interested only in the temperature range from 32° to 95° F., the inventor has generated the following expression which provides an output of ps as a function of F to three significant figures over that temperature range.

$$ps = 35.68e^{\frac{(t-296.65)^2}{-13254}} \qquad \text{Eq. 8}$$

Evaluating the above equation at 90° F. and 55° F., the entering and leaving air conditions, we find:

ps(90° F.)=1.423"Hg ps(55° F.)=0.436"Hg pw, the partial pressure of water in the air in "Hg, is simply RH/100 times the saturation pressure ps of water vapor (HOF 6.12 eq 22) or:

$$pw = ps(RH/100) \qquad \text{Eq.9}$$

Note that the ASHRAE Handbook expresses relative humidity as $\phi$, a fraction, hence the need for dividing RH expressed as a percent by 100.

Having measured relative humidity at 50% for the entering airstream and 90% for the leaving airstream the simple calculation yields:

Inlet Air: pw=1.423(50/100)=0.712"Hg

Discharge Air: pw=0.436(90/100)=0.392"Hg

Now, having in hand the above values of pw and knowing the atmospheric pressure in "Hg, we need only to substitute in the following equation (HOF 6.12 eq.20) to find the humidity ratio W, which we found in the first example at the right hand side of the psychrometric chart.

W (humidity ratio, lb water/lb dry air)=0.622 pw/(p-pw)    Eq.9 where p is the atmospheric pressure in inches Mercury ("Hg) and pw is the partial pressure of the water vapor at the measured condition in "Kg. Evaluating Eq.9 produces:

Inlet Air W=0.0152 lb water/lb dry air

Discharge Air W=0.00826 lb water/lb dry air

A convenient way to measure condensate rate c in the desired units of lb/hr is to measure the time in seconds required to accumulate oz ounces of condensate, calculate oz/sec and multiply the quotient by 225 to get lb/hr.

The air mass flow, from simple stoichiometry, is then:

m=c/(W(in)−W(out)) lb/hr.    Eq.10

Evaluation of which provides the same result as calculation from data derived from the psychrometric chart set forth above.

The enthalpy It of the entering and leaving airstreams employing the humidity ratio W found above and the dry-bulb air temperature t is simply (FOF 6.13 eq 30);

h 0.24t+W(1061+0.444t) Btu/lb    Eq.11

The capacity in Btu/hr is the difference between the enthalpies of the entering and leaving air streams multiplied by the air mass flow in lb/hr.

To calculate CFM from the air mass flow the following formula (HOF 6.13 eq 26) must be evaluated to find the specific volume v in cu ft/lb dry air.

v=0.7543(t+459.7)(1+1.6078W)/p    Eq.12 where t is dry-bulb temperature F, W is humidity ratio and p is atmospheric pressure in inches Mercury. The figure 0.7543 is simply the gas; constant corrected for the units of pressure and the molecular weight of air.

CFM then equals the mass air flow m/60 in pounds per minute times v in cu ft/lb.

The above equations can readily be adapted to a computer program requiring only inputs of the temperature and humidity of the entering and leaving air streams and the condensate rate to secure air flow and coil capacity. Such measurements could be entered into a monitoring program for the purpose of alerting the service group when filters should be changed or of other malfunctions within a complex system.

There are some serious potential pitfalls which can badly distort the results. For example, small condensate flows will limit the reduction in absolute humidity across the coil, thereby resulting in a small absolute humidity difference. Even small errors in measuring the entering and final absolute humidity could then generate very large errors in calculated air-flow and capacity. Also, high air velocities over the cooling coil coupled with a large gap between drain pan and coil can induce high air velocities between the cooling coil and the drain pan, thereby causing condensate to be entrained into the discharge air-stream, rather than falling into the drain pan. If the entrained condensate is re-evaporated into the discharge air stream and therefore can affect the final wet-bulb measurements, the correct results will be( obtained. More likely the entrained condensate will be in a stratum of air which bypasses the wet/dry thermometers/transducers without affecting them, and the results will be skewed.

However, unexpected results will doubtlessly generate thoughtful investigation which will uncover and correct such anomalies thereby providing the customer and user with a better performing system.

From the foregoing description, it can be seen that the present invention comprises an improved method for measurement of dehumidifying coil capacity and air flow and other features. It will be appreciated by those skilled in the art that changes could be made to the embodiments described in the foregoing specification without departing from the broad inventive concept thereof. It is understood, therefore, that this invention is not limited to the particular embodiment or embodiments disclosed, but is intended to cover all modifications which are within the scope and spirit of the invention as defined by the appended claims.

I claim:

1. An entering airstream having a first set of psychrometric conditions, a first heat content, a first moisture content and an airflow rate, cooled heat transfer means positioned in heat transfer relation to said airstream for receiving said entering airstream, removing a quantity of heat at a rate from the airstream and discharging said airstream, whereby the airstream is cooled and moisture is condensed out of said airstream at a rate, thereby providing a flowrate of condensed moisture and a second set of psychrometic conditions in said discharge airstream including a second heat content and a second moisture content, a method for determining the airflow rate of the airstream cooled by the heat transfer element, said method comprising the steps of:

a. measuring a psychrometric condition of the entering airstream from which the moisture content of the entering airstream is determinable, b. measuring a psychrometric condition of the discharge airstream from which the moisture content of the discharge airstream is determinable, c. measuring the condensate flow rate d. determining the moisture content of the entering airstream, determining the moisture content of the discharge airstream and calculating the airflow rate from the condensate flow rate and the moisture contents of the entering and discharge airstreams.

2. A method for measuring the airflow rate as recited in claim 1, further providing the step of displaying the airflow rate.

3. A method for measuring the airflow rate as recited in claim 1, further providing a method for determining the rate of heat removed from said airstream by the cooled heat transfer means, said method comprising the steps of:

a. measuring a psychrometric condition of the entering airstream from which the heat content of the entering airstream is determinable, b. measuring a psychrometric condition of the discharge airstream from which the heat content of the discharge airstream is determinable, c. determining the heat content of the entering airstream, determining the heat content of the discharge airstream and calculating the rate of heat removed from the airstream from the airflow rate and the heat contents of the entering and the discharge airstreams.

4. The method of determining the airflow rate as recited in claim 3, further providing the step of displaying the rate of heat removed from the airstream.

5. A procedure for determining the air flowrate and cooling capacity of a cooling and dehumidifying heat transfer element, said element being subject to an airstream entering, traversing and leaving it, whereby the airstream is cooled and a stream of condensate is produced, comprising the steps of:

measuring the psychrometric conditions of the airstream entering and leaving the heat transfer element and the condensate flowrate, calculating the moisture contents and heat contents of the entering end leaving airstream from the observed psychrometric conditions, calculating the airflow rate and cooling capacity from the moisture contents, the heat contents and the condensate rate.

6. A procedure for determining the air flowrate of an airstream entering, traversing and leaving a cooling and dehumidifying heat transfer element, whereby the airstream is cooled and a stream of condensate is produced, comprising the steps of:

measuring a psychrometric condition of the airstream entering and of the airstream leaving the heat transfer element and the condensate flowrate, calculating the moisture contents of the entering and leaving airstream from the observed psychrometric conditions, calculating the airflow rate from the moisture contents and the condensate rate.

7. A method for determining airflow through an air cooling and dehumidifying coil, said coil having a condensate rate and said coil further having an air stream traversing it and said coil exhibiting a cooling effect on said air stream, said air stream having an inlet condition characteristic of its moisture content before having traversed the coil, an outlet condition characteristic of its moisture content after having traversed the coil and a mass flow, said method comprising the steps of:

determining the condensate rate, determining the inlet condition, determining the outlet condition and calculating the mass air flow from the inlet condition, the outlet condition and the condensate rate.

* * * * *